United States Patent
Pala et al.

(10) Patent No.: US 12,191,035 B1
(45) Date of Patent: Jan. 7, 2025

(54) ADVANCED AUGMENTED ASSISTIVE DEVICE FOR DEMENTIA, ALZHEIMER'S DISEASE, AND VISUAL IMPAIRMENT PATIENTS

(71) Applicants: Nezih Pala, Miami, FL (US); Muhammad Mahmudul Hasan, Miami, FL (US)

(72) Inventors: Nezih Pala, Miami, FL (US); Muhammad Mahmudul Hasan, Miami, FL (US)

(73) Assignee: The Florida International University Board of Trustees, Miami, FL (US)

(*) Notice: Subject to any disclaimer, the term of this patent is extended or adjusted under 35 U.S.C. 154(b) by 0 days.

(21) Appl. No.: 18/664,764

(22) Filed: May 15, 2024

(51) Int. Cl.
  *G16H 40/67* (2018.01)
  *G06F 1/16* (2006.01)
  *G06Q 40/08* (2012.01)
  *G06V 20/20* (2022.01)
  *G16H 20/00* (2018.01)

(52) U.S. Cl.
  CPC .......... *G16H 40/67* (2018.01); *G06F 1/163* (2013.01); *G06Q 40/08* (2013.01); *G06V 20/20* (2022.01); *G16H 20/00* (2018.01)

(58) Field of Classification Search
  CPC ........ G16H 20/00; G16H 40/67; G06F 1/163; G06V 20/20; G06Q 40/08
  USPC ............................................................. 705/2
  See application file for complete search history.

(56) References Cited

U.S. PATENT DOCUMENTS

| 9,694,155 B2* | 7/2017 | Panova ................. G16H 10/60 |
| 2020/0192089 A1* | 6/2020 | Haddick ................ G06F 3/005 |
| 2021/0169417 A1* | 6/2021 | Burton ................ A61B 5/4857 |

FOREIGN PATENT DOCUMENTS

| WO | WO-2020245306 A1 * | 12/2020 | ............. A61N 5/103 |
| WO | WO-2022011233 A1 * | 1/2022 | ............. G06N 3/045 |

OTHER PUBLICATIONS

S00500-021-05701-9.pdf—Muhammad Zahid, Muhammad Attique Khan, Faisal Azam, Muhammad Sharif, Seifedine Kadry, Jnyana Ranjan Mohanty; Pedestrian Identification Using Motion-Controlled Deep Neural Network in Real-Time Visual Surveillance; Soft Computing, Mar. 12, 2021, pp. 453-469 (Year: 2021).*

* cited by examiner

*Primary Examiner* — Karen A Hranek
*Assistant Examiner* — Teresa S Williams
(74) *Attorney, Agent, or Firm* — SALIWANCHIK, LLOYD & EISENSCHENK (57) ABSTRACT

Systems and methods are provided for assisting individuals with physical and/or cognitive ailments, such as dementia, Alzheimer's disease, and/or visual impairment. The quality of life, safety, and/or autonomy of such individuals can be enhanced by utilizing a combination of sensors, actuators, augmented reality (AR) technology, and machine learning (ML) algorithms. The sensors and actuators can include (but are not limited to) cameras, global positioning system (GPS) sensors, accelerometers, motion sensors, AR visual systems, headphones, microphones, haptic feedback systems, and/or connectivity capabilities (wired and/or wireless) to provide information about the surrounding environment and events. By leveraging advanced sensor technology, AR, and real-time data processing, a comprehensive support system can be provided that addresses the unique challenges faced by these individuals on a daily basis.

13 Claims, 10 Drawing Sheets

ADVANCED AUGMENTED ASSISTIVE DEVICE FOR DEMENTIA, ALZHEIMER'S DISEASE, AND VISUAL IMPAIRMENT PATIENTS

BACKGROUND

Navigating daily life can be difficult for individuals with certain physical and/or cognitive ailments, such as dementia, Alzheimer's disease, and/or visual impairment. Such individuals may have difficulty with navigation, social interaction, health monitoring, or health care.

BRIEF SUMMARY

Embodiments of the subject invention provide novel and advantageous systems and methods for assisting individuals with certain ailments (e.g., physical and/or cognitive ailments, such as dementia, Alzheimer's disease, and/or visual impairment) in their daily activities. The quality of life, safety, and/or autonomy of such individuals can be enhanced by utilizing a combination of sensors (e.g., cutting-edge sensors), actuators, augmented reality (AR) technology, and/or artificial intelligence (AI)/machine learning (ML) algorithms. The sensors and actuators can include (but are not limited to) wearable sensors for physiological parameters and vital signs, cameras, global positioning system (GPS) sensors, accelerometers, motion sensors, AR visual systems, headphones, microphones, haptic feedback systems, and/or connectivity capabilities (wired and/or wireless) to provide information about the surrounding environment and events. By leveraging advanced sensor technology, AR, and real-time data processing, a comprehensive support system can be provided that addresses the unique challenges faced by these individuals on a daily basis. Systems and methods can be useful for individuals with dementia, individuals with Alzheimer's disease, individuals with visual impairments, caregivers, healthcare providers, and insurance companies who can benefit from better control over insurance plans and access to valuable user data.

In an embodiment, a system for assisting a subject with an ailment can comprise: at least one camera; at least one gyroscope; at least one AR device (e.g., smart glasses, smart watch, and/or smart shoes); at least one biometric sensor; at least one processor in operable communication with the at least one camera, the at least one gyroscope, the at least one AR device, and the at least one biometric sensor; and a machine-readable medium in operable communication with the processor and having instructions stored thereon that, when executed by the processor, perform the following steps: a) receiving input data about the subject and a surrounding area of the subject, the input data comprising data received from the at least one camera, the at least one gyroscope, and the at least one biometric sensor; b) utilizing an ML (and/or AI) algorithm on the input data to analyze at least one of objects, people, conditions, and events in the surrounding area of the subject and generate an action plan to assist the subject; and c) providing the action plan to the subject via at least one of visual feedback to the subject, audio feedback to the subject, and haptic feedback to the subject. The providing of the action plan can comprise using the at least one AR device (e.g., via a display that is part of the AR device). The system can further comprise at least one microphone in operable communication with the processor, and the input data can further comprise data received from the at least one microphone. The system can further comprise: an accelerometer in operable communication with the processor; and/or a heart rate sensor in operable communication with the processor. The input data can further comprise data received from the accelerometer and/or data received from the heart rate sensor. The system can further comprise at least one audio output device (e.g., headphones, a headset, and/or a set of earbuds (any of which can be wireless or wired)) in operable communication with the processor. The providing of the action plan can comprise using the at least one audio output device. The system can further comprise at least one haptic actuator in operable communication with the processor, and the providing of the action plan can comprise using the at least one haptic actuator. The system can further comprise at least one GPS sensor in operable communication with the processor, and the input data can further comprise data received from the at least one GPS sensor. The ML algorithm can comprise, for example, a convolutional neural network (CNN), a recurrent neural network (RNN), a graph neural network (GNN), a variational autoencoder (VAE), a generative adversarial network (GAN), a natural language processing (NLP) model, a large language model (LLM), a multimodal large language model (MLLM), a natural language understanding (NLU) model, a time series analysis model, and/or a classification model. The instructions when executed can further perform the step of d) transmitting, to an insurance company, at least one of: the input data; and output data generated by the ML model based on the analyzing of at least one of objects, people, conditions, and events in the surrounding area of the subject. The action plan can be, for example, an action plan for wayfinding, social interaction, situational awareness, health monitoring, emotional state management, and/or medication and appointment management. The ailment can be, for example, dementia, Alzheimer's disease, and/or visual impairment.

In another embodiment, a method for assisting a subject with an ailment can comprise: a) receiving (e.g., by a processor) input data about the subject and a surrounding area of the subject, the input data comprising data received from at least one camera, at least one gyroscope, and at least one biometric sensor; b) utilizing (e.g., by the processor) an ML (and/or AI) algorithm on the input data to analyze at least one of objects, people, conditions, and events in the surrounding area of the subject and generate an action plan to assist the subject; and c) providing (e.g., by the processor) the action plan to the subject via at least one of visual feedback to the subject, audio feedback to the subject, and haptic feedback to the subject. The providing of the action plan can comprise using at least one AR device worn by the subject (e.g., via a display that is part of the AR device). The input data can further comprise data received from at least one microphone. The input data can further comprise data received from at least one GPS sensor. The input data can further comprise data received from an accelerometer and/or data received from a heart rate sensor. The providing of the action plan can comprise using at least one audio output device (e.g., headphones, a headset, and/or a set of earbuds (any of which can be wireless or wired)). The providing of the action plan can comprise using at least one haptic actuator. The ML algorithm can comprise, for example, a CNN, a RNN, a GNN, a VAE, a GAN, an NLP model, an LLM, an MLLM, an NLU model, a time series analysis model, and/or a classification model. The method can further comprise: d) transmitting (e.g., by the processor), to an insurance company, at least one of: the input data; and output data generated by the ML model based on the analyzing of at least one of objects, people, conditions, and events in the surrounding area of the subject. The action plan can be an action plan for wayfinding, social interaction, situational awareness, health monitoring, emotional state management, and/or medication and appointment management. The ailment can be, for example, dementia, Alzheimer's disease, and/or visual impairment. Any or all of the devices for collecting input data or providing the action plan can be in operable communication with the processor.

BRIEF DESCRIPTION OF DRAWINGS

FIG. 1 depicts a general case for the system.

FIG. 2 depicts the case where the system assists with address recall, location sharing, and wayfinding.

FIG. 3 depicts the case where the system assists with social interaction.

FIG. 2 depicts the case where the system assists with contextual and situation awareness.

FIG. 5 depicts the case where the system assists with activity and health monitoring.

FIG. 6 depicts the case where the system collects health-related data from the user and provides it to a caregiver and/or an insurance company (e.g., after processing through a machine learning (ML) model).

FIG. 7 depicts the case where the system assists with emotional state management.

FIG. 8 depicts the case where the system assists with medication and appointment management.

FIG. 9 depicts the inputs and outs integrated with the user's body.

DETAILED DESCRIPTION

Embodiments of the subject invention provide novel and advantageous systems and methods for assisting individuals with certain ailments (e.g., physical and/or cognitive ailments, such as dementia, Alzheimer's disease, and/or visual impairment) in their daily activities. The quality of life, safety, and/or autonomy of such individuals can be enhanced by utilizing a combination of sensors (e.g., cutting-edge sensors), actuators, augmented reality (AR) technology, and/or artificial intelligence (AI)/machine learning (ML) algorithms. The sensors and actuators can include (but are not limited to) wearable sensors for physiological parameters and/or vital signs, cameras, global positioning system (GPS) sensors, motion sensors, accelerometers, AR visual systems, headphones, microphones, haptic feedback systems, and/or connectivity capabilities (wired and/or wireless) to provide information about the surrounding environment and events. By leveraging advanced sensor technology, AR, and real-time data processing, a comprehensive support system can be provided that addresses the unique challenges faced by these individuals on a daily basis. Systems and methods can be useful for individuals with dementia, individuals with Alzheimer's disease, individuals with visual impairments, caregivers, healthcare providers, and insurance companies who can benefit from better control over insurance plans and access to valuable user data.

Figure 1:
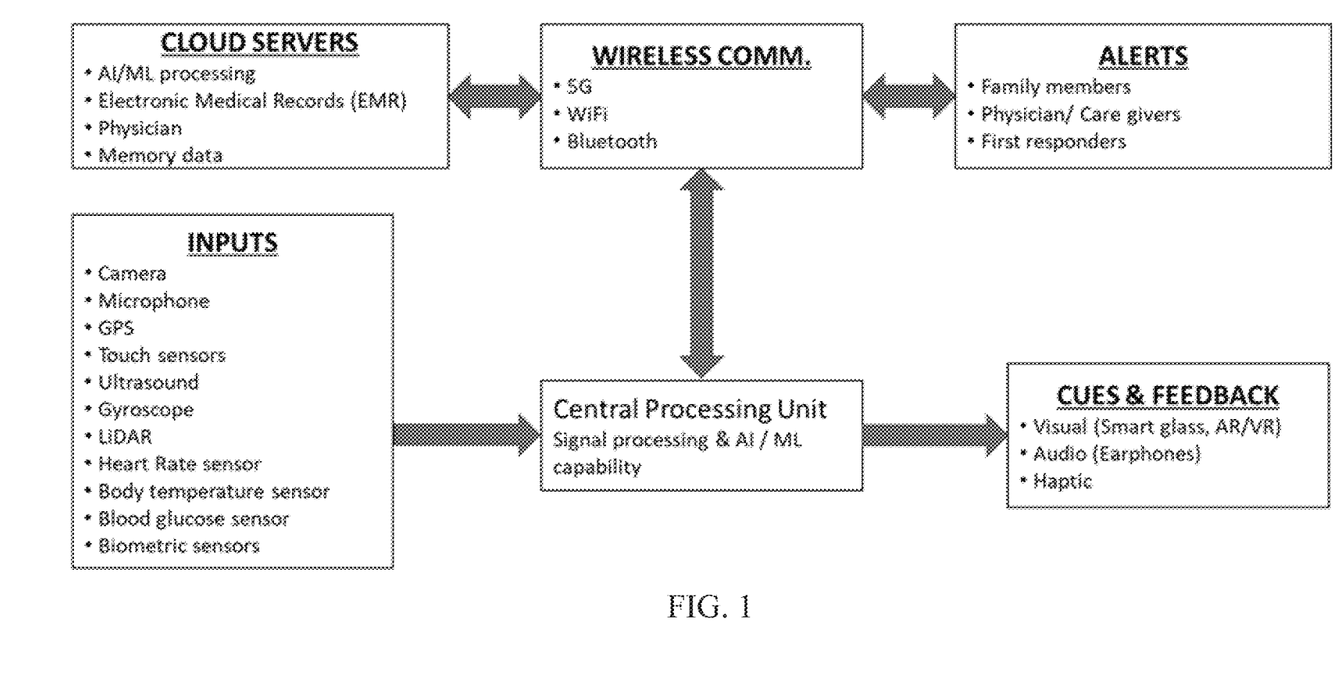
FIG. 1 shows a block diagram of a system for assisting individuals with certain ailments (e.g., physical and/or cognitive ailments, such as dementia, Alzheimer's disease, and/or visual impairment), according to an embodiment of the subject invention.

Systems and methods of embodiment of the subject invention can use a plurality of sensors to collect input data to analyze objects, people, conditions, and/or events in the surroundings of the user using AI and/or ML algorithms and provide output information to the user via visual, audio, and/or haptic means for assistance. An important feature is the generation of specific action plans for the user for emerging situations and acting accordingly. Each event can be identified and required command prompts can be provided to the user utilizing one sensor or a combination of multiple sensors and actuators. FIG. 1 shows a block diagram of a system for assisting individuals with certain ailments, according to an embodiment of the subject invention. FIG. 1 shows examples of many types of cloud servers, wireless communications, alerts, inputs, and cues/feedback that can be present. The system need not include all of the items listed in FIG. 1; they are listed for exemplary purposes.

Figure 2:
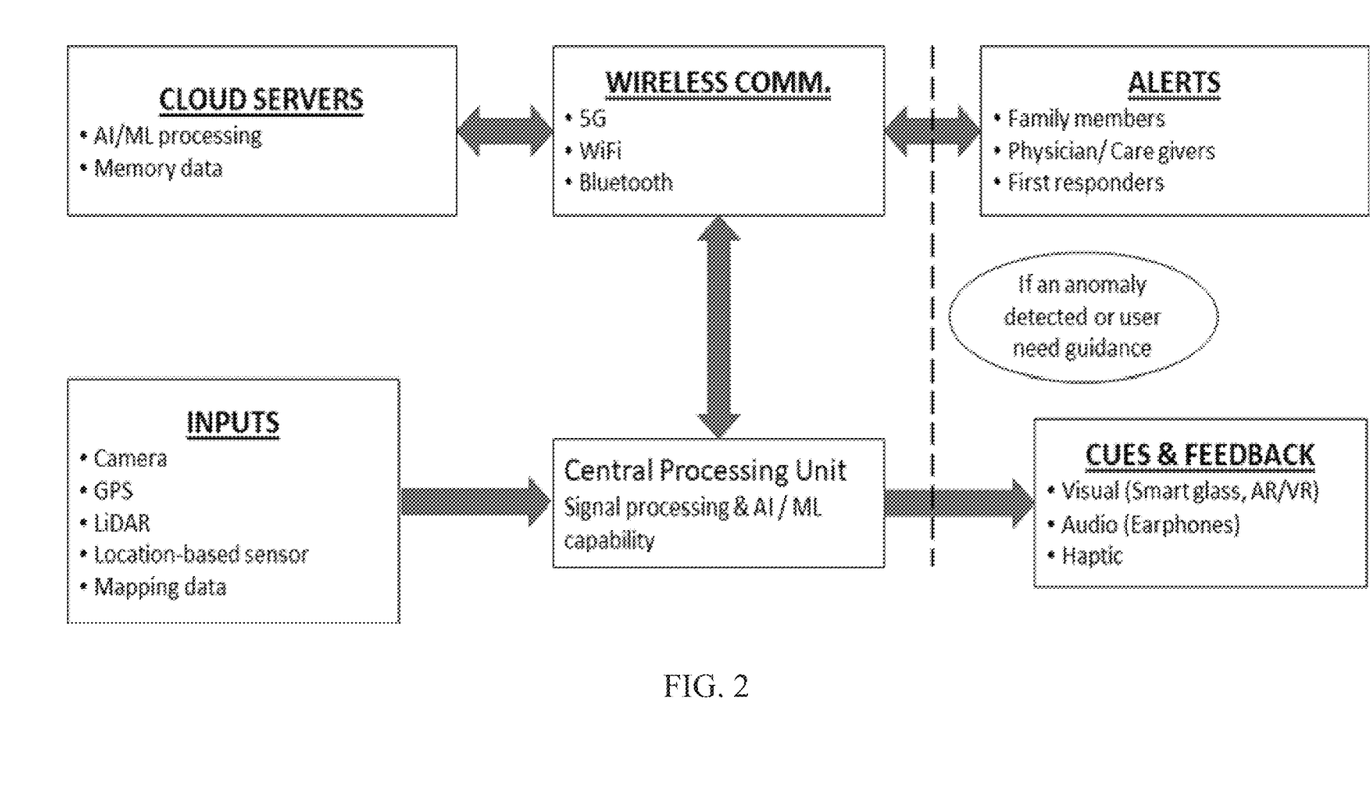
FIG. 2 shows a block diagram of a system for assisting individuals with certain ailments, according to an embodiment of the subject invention.

FIG. 2 shows a block diagram of a system in the scenario of assisting with address recall, location sharing, and wayfinding. The system can have access to the regular routine and/or travel itineraries of the user. It can detect anomalies or unexpected trips using AI and/or ML support and guide the user accordingly. The system can utilizes a combination of GPS (and/or other location-based sensors), mapping data, and cameras to determine the user's current location, provide address recall assistance, and enable wayfinding capabilities. The AR display on the smart glasses or headset of the system can guide the user with visual cues, while audio cues can be provided (e.g., for visually impaired users). The system can also share the user's location with designated caregivers and/or healthcare providers, allowing them to monitor the user's whereabouts and ensure their safety. For example, the system can provide step-by-step guidance for a user to go to a market for shopping. If the user takes public transportation, the system can guide the user to the station or the stop, remind the user of the number of the bus or train to get on, and/or remind the user again to get off when arriving at the destination stop. AI and ML algorithms, tools, and techniques (existing and/or newly-developed) can be used for this scenario and the other example scenarios (as described herein).

For example, a model for natural language understanding (NLU) (or a large language model (LLM) or a multimodal large language model (MLLM)) can be used, possibly bidirectional encoder representations from transformers (BERT) or generative pre-trained transformer (GPT) to get user commands and understand queries about the address, location, and transportation (see also; Jiao et al., Tinybert: Distilling bert for natural language understanding, arXiv preprint arXiv:1909.10351, 2019; and Liu et al., GPT understands, too, AI Open, 2023; both of which are hereby incorporated by reference herein in their entireties).

As for anomaly detection in the case of user's travel patterns or routines, which is a time-series data, a recurrent neural network (RNN) model with long short term memory (LSTM) networks can be used (see also; Sherstinsky, Fundamentals of recurrent neural network (RNN) and long short-term memory (LSTM) network, Physica D: Nonlinear Phenomena 404, 2020, 132306; which is hereby incorporated by reference herein in its entirety). LSTM networks are a type of RNN that are well matched for anomaly detection in sequential data when ordering events. The macroscopic workflow of the model can be as follows.

Data preparation: Collection of user's previous travel patterns, plans, and routines along with the location, timestamps, and modes of transportation.

Feature selection: Identifying the relevant features from the huge data, like time, location, trip duration, frequency of identical trips, etc.

Model training: Training of the LSTM RNN model using the prepared dataset. It learns the usual travel behavior along with the variation in user's travel patterns and gains the ability to predict the next event.

Anomaly detection and response: The model can then detect any significant deviation from the expected pattern. Depending on the set threshold level of acceptable deviation, the model can trigger an alert to notify the caregivers of healthcare providers.

Figure 3:
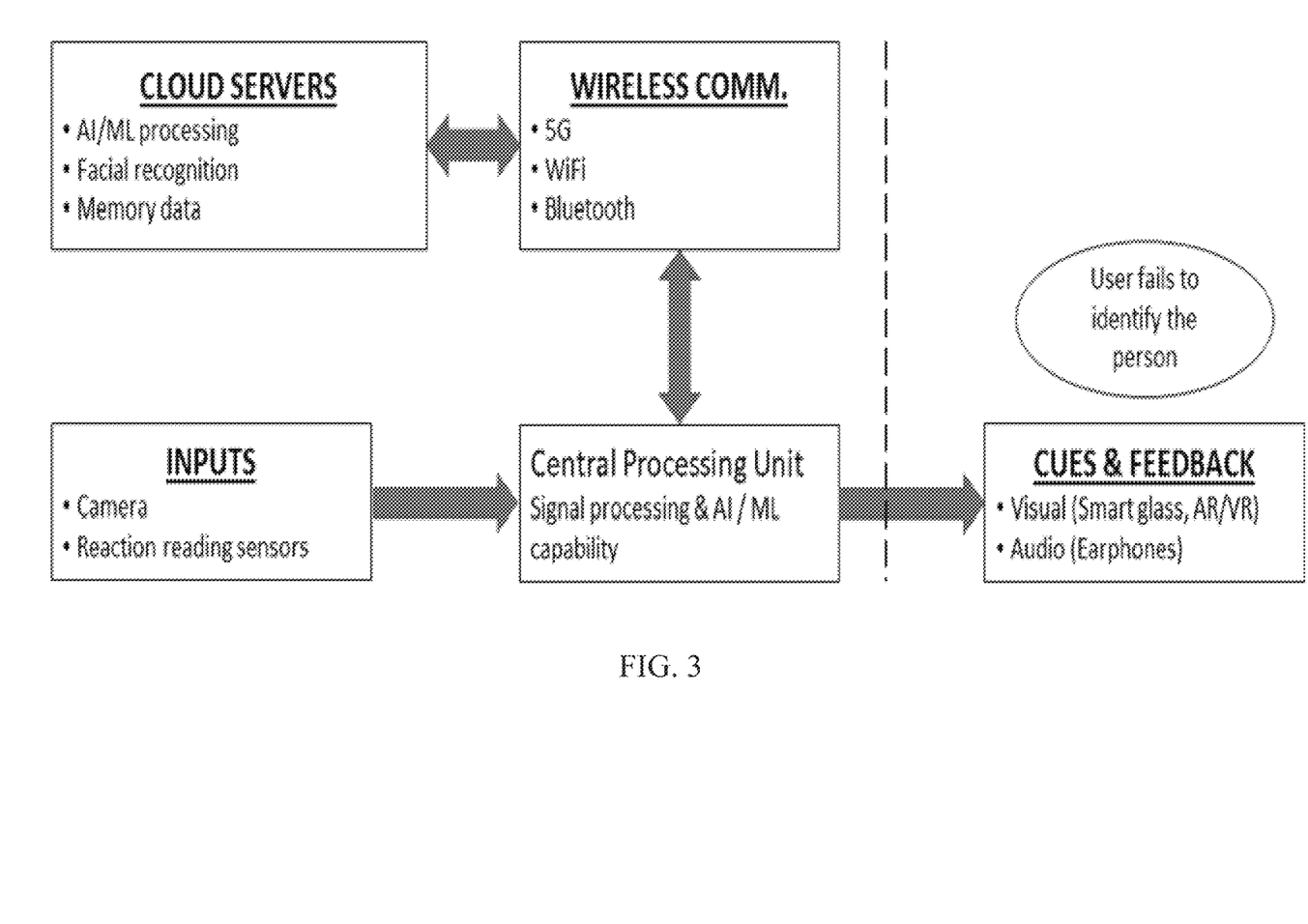
FIG. 3 shows a block diagram of a system for assisting individuals with certain ailments, according to an embodiment of the subject invention.

FIG. 3 shows a block diagram of a system in the scenario of assisting with social interaction (i.e., enhanced facial recognition and social interaction assistance). The system can employ advanced facial recognition technology, ML algorithms, and a customizable database of familiar people to help users with dementia or Alzheimer's identify those around them more accurately. The system can detect the situation by analyzing the user's reaction using AI when the user can't identify the people around him or her. The AR smart glasses can display the names, relationships, and contextual information (e.g., last interaction, shared memories) of recognized individuals, assisting the user in social interactions and fostering better emotional connections. For visually impaired users, the system can provide audio cues to notify them of familiar individuals in their surroundings. The situation can be managed using a combination of facial recognition model, emotion recognition model, and contextual understanding model.

With respect to a facial recognition model, convolutional neural network (CNN)-based deep learning models can be a good match for this situation. There are already established models like VGG-Face, Facenet, and ArcFace for accurate and fast facial recognition (see also; Cao et al., Vggface2: A dataset for recognising faces across pose and age, 2018 13th IEEE international conference on automatic face & gesture recognition, FG 2018, IEEE, 2018; Schroff et al., Facenet: A unified embedding for face recognition and clustering, Proceedings of the IEEE conference on computer vision and pattern recognition, 2015; and Deng et al., Arcface: Additive angular margin loss for deep face recognition, Proceedings of the IEEE/CVF conference on computer vision and pattern recognition, 2019; all three of which are hereby incorporated by reference herein in their entireties). The system can use one of those models in certain embodiments. The model workflow can start with a CNN architecture trained on a diverse dataset of labeled facial images. The model gains the ability to identify distinct features on faces and create compact embeddings that represent each person during training. By comparing the embeddings of newly discovered faces to a database of known people, inference determines recognition based on similarity metrics. Real-time processing optimization ensures quick identification of the user's surroundings.

With respect to the emotion recognition model, it can be use CNNs or RNNs trained on a dataset of facial images labeled with emotion categories (see also; Lim, Speech emotion recognition using convolutional and recurrent neural networks, 2016 Asia-Pacific signal and information processing association annual summit and conference (APSIPA), IEEE, 2016; and Jain et al., Hybrid deep neural networks for face emotion recognition, Pattern Recognition Letters 115, 2018, 101-106; both of which are hereby incorporated by reference herein in their entireties). The model gains the ability to identify facial expressions that correspond to various emotions throughout training. The model predicts the most likely emotion conveyed in a new face image. Real-time processing optimization ensures efficient and timely recognition of emotional states.

With respect to contextual understanding, a graph neural network (GNN) is typically used in social interaction context (see also; Fan et al., Graph neural networks for social recommendation, The world wide web conference, 2019; which is hereby incorporated by reference herein in its entirety). The model can analyze relationships, interactions, and shared memories among individuals. When combined with the facial recognition technology and emotion recognition model, it offers insightful context in addition to identification outcomes, making it easier for those suffering from dementia or Alzheimer's to comprehend and interact with others.

Figure 4:
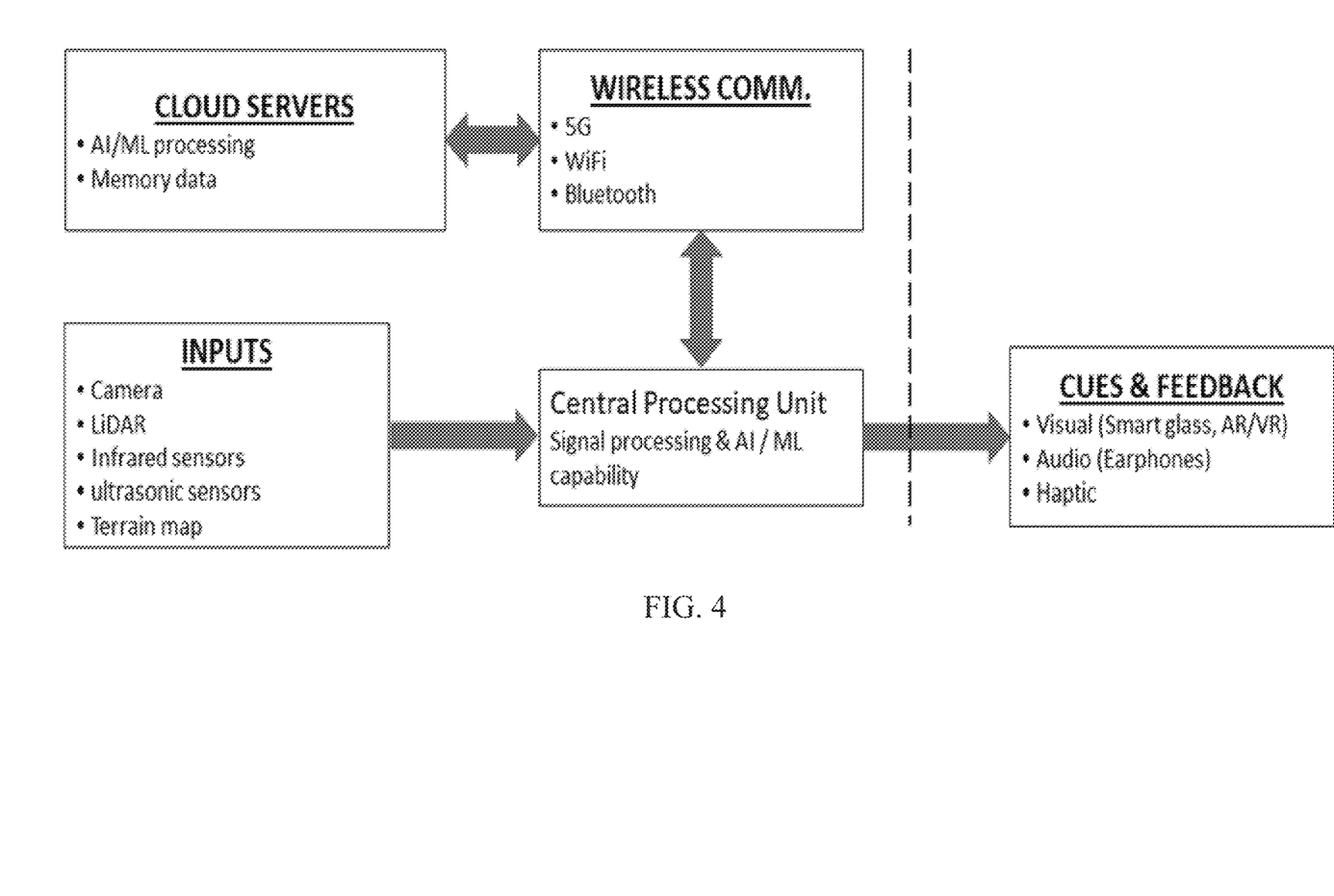
FIG. 4 shows a block diagram of a system for assisting individuals with certain ailments, according to an embodiment of the subject invention.

FIG. 4 shows a block diagram of a system in the scenario of contextual and situational awareness. The system can integrate various sensors, such as a LiDAR (light detection and ranging) sensor, an infrared (IR) sensor, an ultrasonic sensor, a camera, and/or a terrain map to create comprehensive situational awareness for users with dementia, Alzheimer's, or visual impairments. These sensors detect obstacles, changes in terrain, nearby moving objects, and other potential hazards, providing real-time information to the user through the AR display or audio cues as shown in FIG. 4. The system can also adapt its assistance based on the user's specific needs and preferences, thanks to its ML capabilities. A combination of sensor fusion and environment perception model can be used to assess the situation and environment around the user. An adaptive assistance model can also be used to personalize the system's assistance according to the user's needs and preferences.

With respect to the sensor fusion and environmental perception model, CNNs can be used to process the visual data from the cameras while RNNs can manage the time series data coming from different sensors to assess the surroundings (see also; Uddin et al., A body sensor data fusion and deep recurrent neural network-based behavior recognition approach for robust healthcare, Information Fusion 55, 2020, 105-115; which is hereby incorporated by reference herein in its entirety). Also, an object detection and tracking model, such as region-based convolutional neural network (R-CNN), can be utilized to track the nearby moving objects and predict their trajectories (see also; Girshick, Fast r-cnn, Proceedings of the IEEE international conference on computer vision, 2015; which is hereby incorporated by reference herein in its entirety). Eventually, a deep-learning-based fusion approach can be implemented to create a unified representation of the surroundings.

With respect to the adaptive assistive model, reinforcement learning (RL) can be used to adaptively adjust assistance based on user needs and preferences, while context-aware decision-making models (e.g., deep Q-learning) can include environmental and user-specific factors in decision processes (see also; Yu et al., Reinforcement learning in healthcare: A survey, ACM Computing Surveys (CSUR) 55.1, 2021, 1-36; and Konar et al., A deterministic improved Q-learning for path planning of a mobile robot, IEEE Transactions on Systems, Man, and Cybernetics: Systems 43.5, 2013, 1141-1153; both of which are hereby incorporated by reference herein in their entireties). Additionally, personalized assistance models can continually learn from user feedback to tailor behavior over time.

Figure 5:
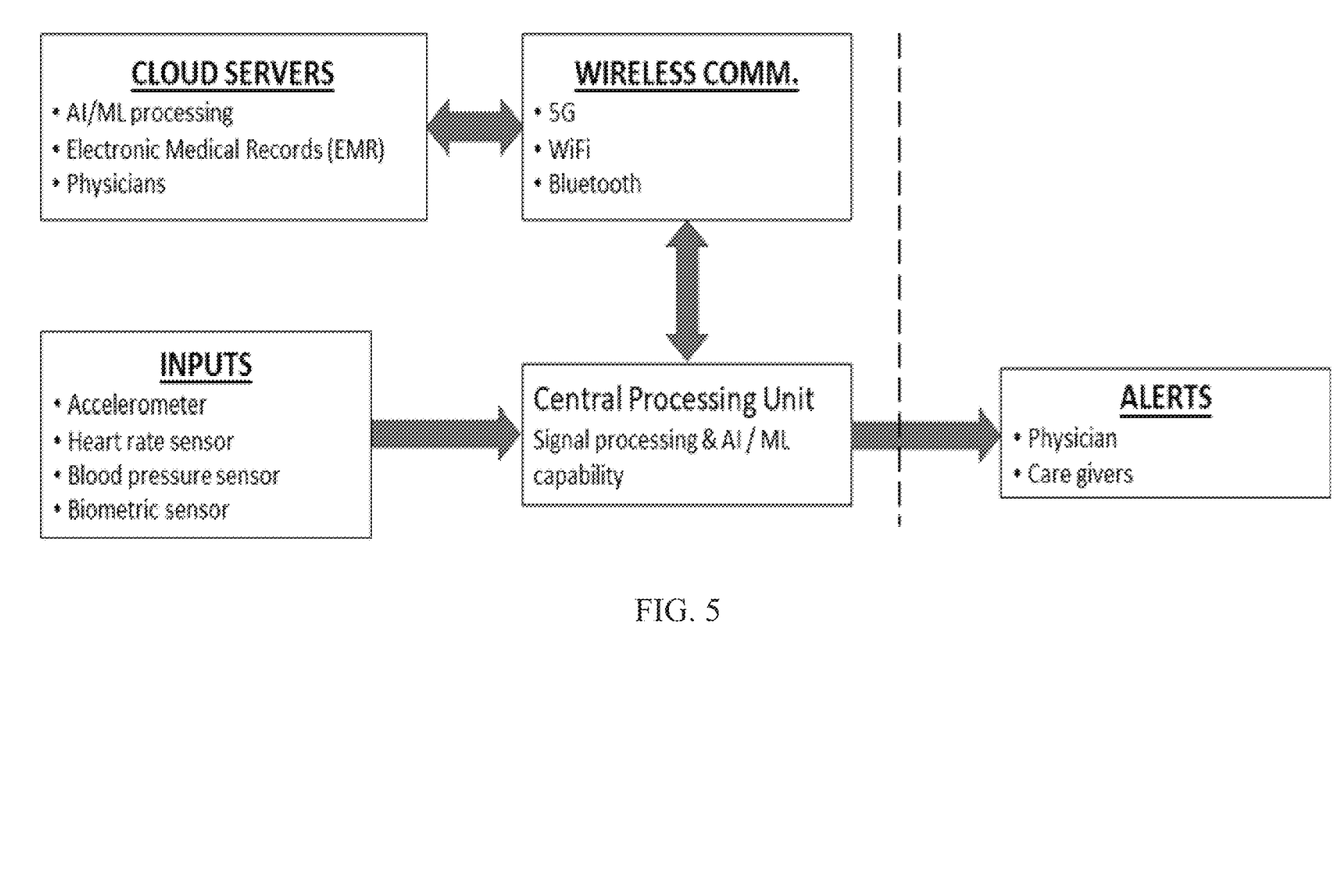
FIG. 5 shows a block diagram of a system for assisting individuals with certain ailments, according to an embodiment of the subject invention.

FIG. 5 shows a block diagram of a system in the scenario of activity and health monitoring. The system can incorporate activity tracking and health monitoring features, such as an accelerometer and heart rate sensor, to help users maintain a healthy lifestyle and provide caregivers or healthcare providers with essential health data. This information can be used to detect potential health issues, track the progression of dementia or Alzheimer's, and tailor care plans accordingly.

Figure 6:
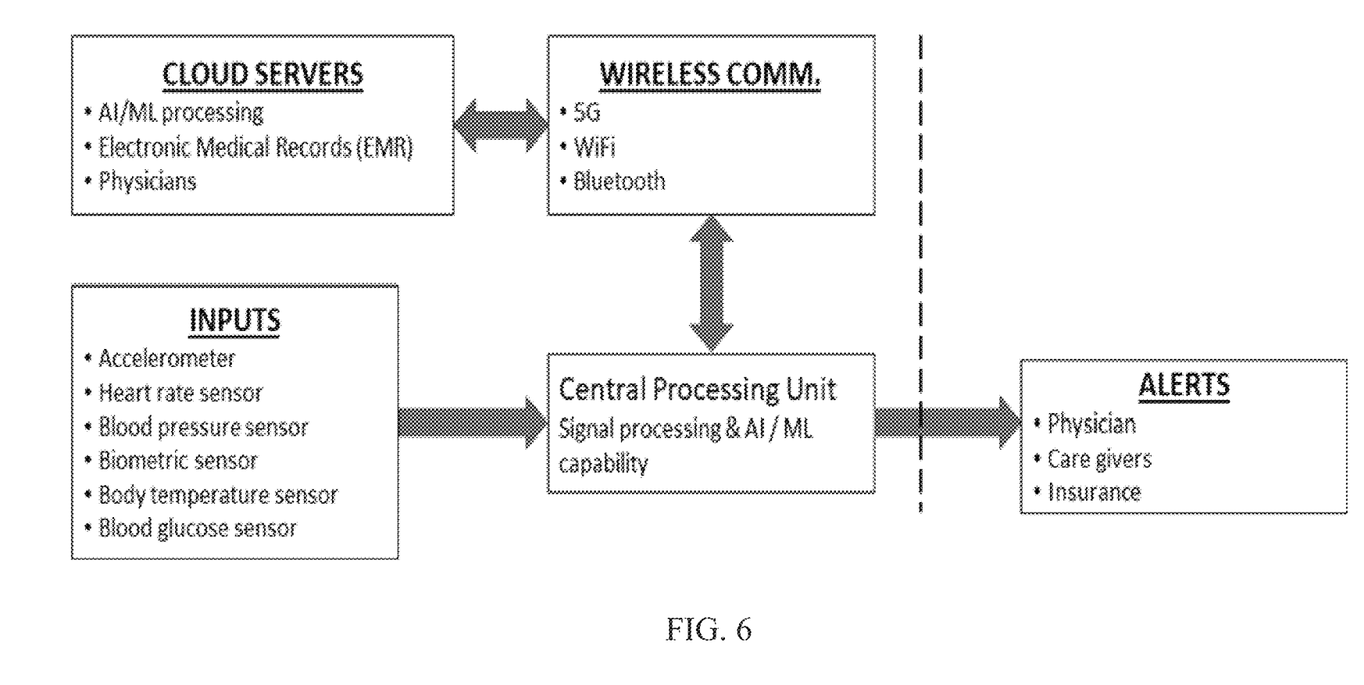
FIG. 6 shows a block diagram of a system for assisting individuals with certain ailments, according to an embodiment of the subject invention.

FIG. 6 shows a block diagram of a system in the scenario of integration with insurance companies and healthcare providers. The system can provide valuable data to insurance companies and healthcare providers, allowing them to have better control over insurance plans, assess risk factors, and make informed decisions about patient care. By monitoring the user's health, activity, and situational awareness, these organizations can adjust their plans, premiums, and interventions accordingly, potentially leading to cost savings, improved care, and better outcomes for clients. The system's ability to track health metrics and detect potential issues early can aid healthcare professionals in providing timely and effective interventions for their patients. Also, the system can provide valuable support, reduce the burden on caregivers, and offer peace of mind by monitoring the user's well-being and location. FIG. 6 shows the flow diagram of collecting the health-related data from the user and providing it to the caregivers and insurance after processing through AI/ML models. AI models such as time series analysis techniques (e.g., autoregressive integrated moving average (ARIMA) or seasonal decomposition of time series (STL)) can be implemented to detect patterns and trends in data from sensors like accelerometers and heart rate monitors to keep track of a user's dementia or Alzheimer's (see also; Schaffer et al., Interrupted time series analysis using autoregressive integrated moving average (ARIMA) models: a guide for evaluating large-scale health interventions, BMC medical research methodology 21, 2021, 1-12; and Ordu et al., A comprehensive modelling framework to forecast the demand for all hospital services, The International Journal of Health Planning and Management 34.2, 2019, e1257-e1271; both of which are hereby incorporated by reference herein in their entireties). Classification models (e.g., support vector machines (SVMs) or random forests) can be utilized to classify the activity data into different categories like sedentary activity and moderate activity, and heart rate data into different zones like resting and vigorous intensity (see also; Nagendra et al., Evaluation of support vector machines and random forest classifiers in a real-time fetal monitoring system based on cardiotocography data, 2017 IEEE conference on computational intelligence in bioinformatics and computational biology (CIBCB), IEEE, 2017; which is hereby incorporated by reference herein in its entirety). Health risk assessment models (e.g., logistic regression or gradient boosting machines) can evaluate the user's risk of health conditions or adverse events, assisting caregivers and healthcare providers in interventions (see also; Xu et al., Extreme gradient boosting model has a better performance in predicting the risk of 90-day readmissions in patients with ischaemic stroke, Journal of Stroke and Cerebro-vascular Diseases 28.12, 2019, 104441; which is hereby incorporated by reference herein in its entirety).

Figure 7:
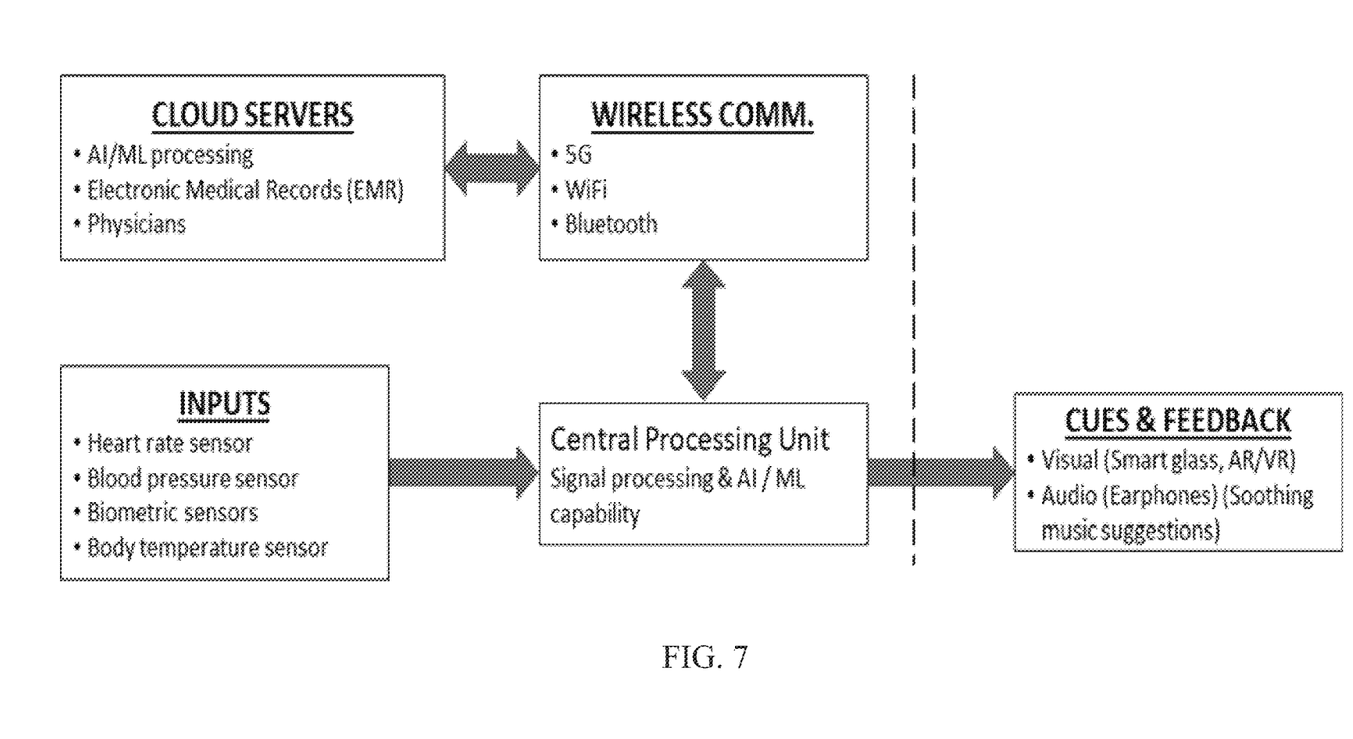
FIG. 7 shows a block diagram of a system for assisting individuals with certain ailments, according to an embodiment of the subject invention.

FIG. 7 shows a block diagram of a system in the scenario of emotional support. By monitoring the user's emotional state through biometric sensors, the system can provide personalized coping strategies, soothing music, and/or reminders to practice mindfulness and relaxation techniques during times of stress or anxiety. At first the emotional status of the user can be determined using help from the emotion recognition model described for the scenario of assisting with social interaction. Additionally, biometric sensor data can also be analyzed to determine the emotional state. Next, RL can be used to select the adaptive personalized recommendations (see also Yu et al., supra.). Natural language processing (NLP) can be utilized to analyze the input from the user and extract the sentiment and context. In this way the model can provide customized responses and supportive messages for coping strategies. In addition, variational autoencoders (VAEs) or generative adversarial networks (GANs) can be implemented to generate tailored soothing music according to the emotional state of the user (see also; Welikala et al., Komposer v2: A hybrid approach to intelligent musical composition based on generative adversarial networks with a variational autoencoder, Proceedings of the Future Technologies Conference (FTC) 2020, Volume 1, Springer Inter-national Publishing, 2021; which is hereby incorporated by reference herein in its entirety).

Figure 8:
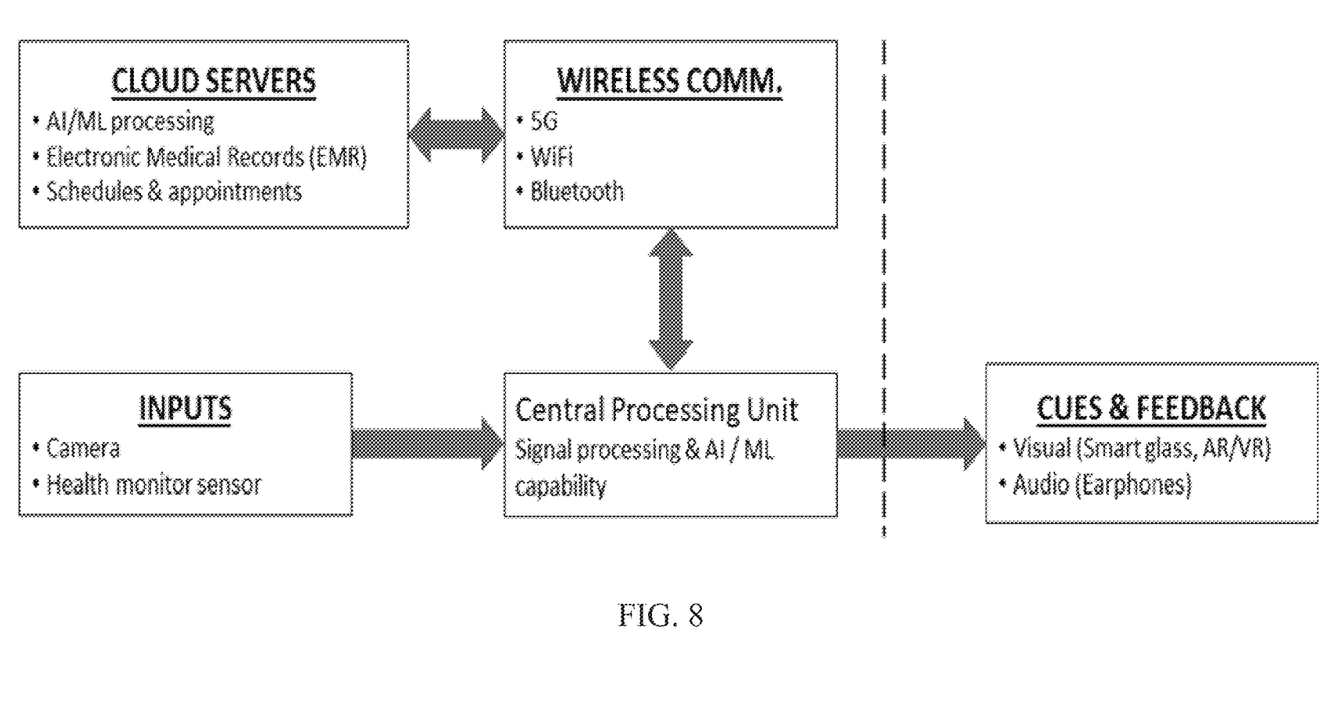
FIG. 8 shows a block diagram of a system for assisting individuals with certain ailments, according to an embodiment of the subject invention.

FIG. 8 shows a block diagram of a system in the scenario of medication and appointment reminders. The system can remind users to take their medications, attend appointments, and/or complete other essential tasks, ensuring they adhere to their care plans and maintain their health. A combination of RNNs and GNNs can be used for time series analysis of daily routine, appointment schedules, etc. and to model the relationship between the medications, appointments, and other schedules (see also; Jain et al., supra.; and Fan et al., supra.). In this way the model can learn the daily routine, doctor's appointments, and medication time and find the conflicting schedules. NLP and/or RL models can be implemented to analyze the user input and provide adaptive responses and reminders (see also, Yu et al., supra.).

In certain cases, the user might be sensitive to certain gases, particulates, air pollutants, and similar matter. For such users, the system can include sensors to detect such matter and warn the user. This data can be complemented or substituted with geospatial data (e.g., pollen maps) when available. This can includes sensor fusion with deep learning (e.g., RNN), anomaly detection models (e.g., LSTM), integration of geospatial data, predictive modeling for pollution forecasting, and/or personalized alerting systems (e.g., RL) (see also; Jain et al., supra.; Sherstinsky, supra.; and Yu et al., supra.). By leveraging these AI models, the system can effectively monitor environmental conditions and provide timely warnings to sensitive users, allowing them to take proactive measures to protect their health.

Figure 9:
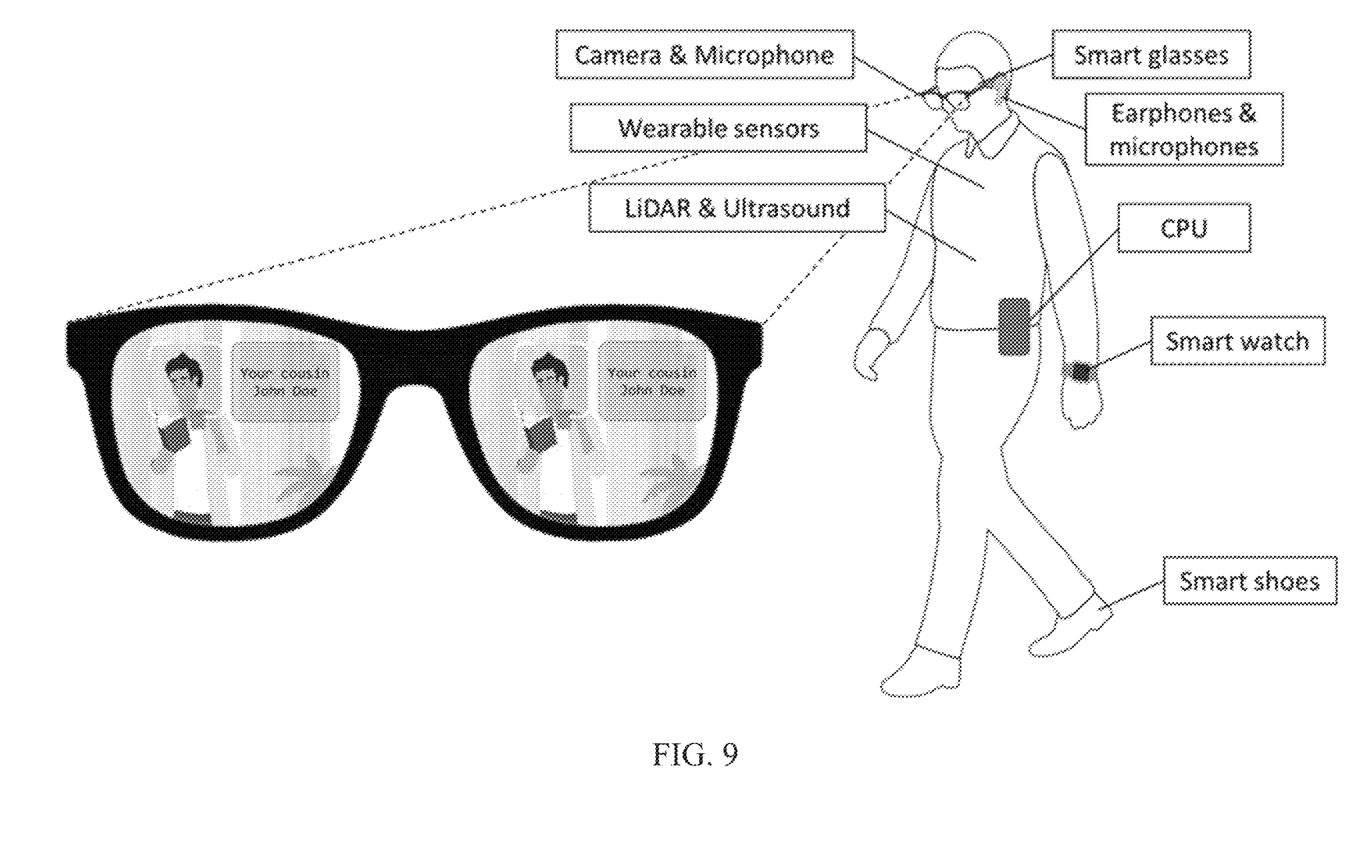
FIG. 9 shows a schematic view of inputs and outputs of a system for assisting individuals with certain ailments, according to an embodiment of the subject invention.

Referring to FIG. 9 (and again to FIG. 1), embodiments of the subject invention can include a wide array of components and technologies, including but not necessarily limited to one or more of: at least one accelerometer; GPS and/or geofencing; at least one integrated camera; at least one set of headphones; at least one microphone; at least one haptic sensor; at least one haptic actuator; at least one AR device; at least one other type of sensor (e.g., environmental sensor and/or biometric sensor); at least one other type of actuator; ML and/or AI; and/or data storage. These are described in more detail below.

Accelerometer: An accelerometer can be used to monitor user movement, allowing the system to tailor its assistance based on the user's activities, habits, and/or mobility patterns. Many smartwatches and smartphones have accelerometers.

GPS and geofencing: Integrated GPS technology can enables location-based assistance while geofencing features can alert caregivers if users wander outside of designated safe zones. Most modern devices have GPS integrated therein.

Integrated camera: A camera or a network of multiple cameras (or camera systems) can help create a memory lane for the user by developing a database of close people and familiar locations. This can enable the facial recognition process to identify family members, caregivers, and healthcare providers around a user (e.g., a user with dementia or Alzheimer's). An integrated camera (or camera system) can also acquire real-time data, which can help to detect immediate threats and potential hazards.

Headphones: Headphones, headsets, and/or earbuds (wired or wireless) can provide timely audio cues about the surrounding environments or any obstacles in case of a user with visual impairment. They can also provide emotional support in times of stress by playing music or other relaxation sounds selected through AI/ML processing.

Microphone: At least one microphone can collect audio data of the surroundings and the voice of familiar people including family members and health care providers of the user. This data can be stored in a cloud or local storage for further processing.

Haptic sensor: When the system detects an anomaly in the user's health monitoring system, an obstacle in the surroundings, or any other situation where the user (visually and/or audibly impaired) needs to be alerted, the at least one haptic sensor can be triggered.

Haptic actuator: These actuators can act depending on the signals that come from the haptic sensor(s). Haptic actuators can help those who have visual and/or auditory challenges to recreate the environment around them using vibrations and/or other haptic feedback systems. They can also alert users in case of emergency movements (see also Liu et al., supra.).

AR device: Smart glasses and/or headsets equipped with AR technology can offer users visual and/or audio cues related to their environment, providing contextually relevant information (see also; Sherstinsky, supra.; and Cao et al., supra.).

Other sensors and actuators: A combination of environmental and/or biometric sensors can gather data about the user's surroundings, physical condition, and/or emotional state, ensuring personalized and timely support. Wearable biometric sensors can collect not only physical data but also emotional state data (see also; Schroff et al., supra.; and Deng et al., supra.). Also, some technologies integrated with smartwatches claim to be able to sense human emotional state (see also, Lim et al., supra.).

ML and AI: The system can utilize AI and ML algorithms to analyze data, recognize patterns, and adapt its assistance to each user's specific needs. Specific models have been described herein for different scenarios.

Figure 10:
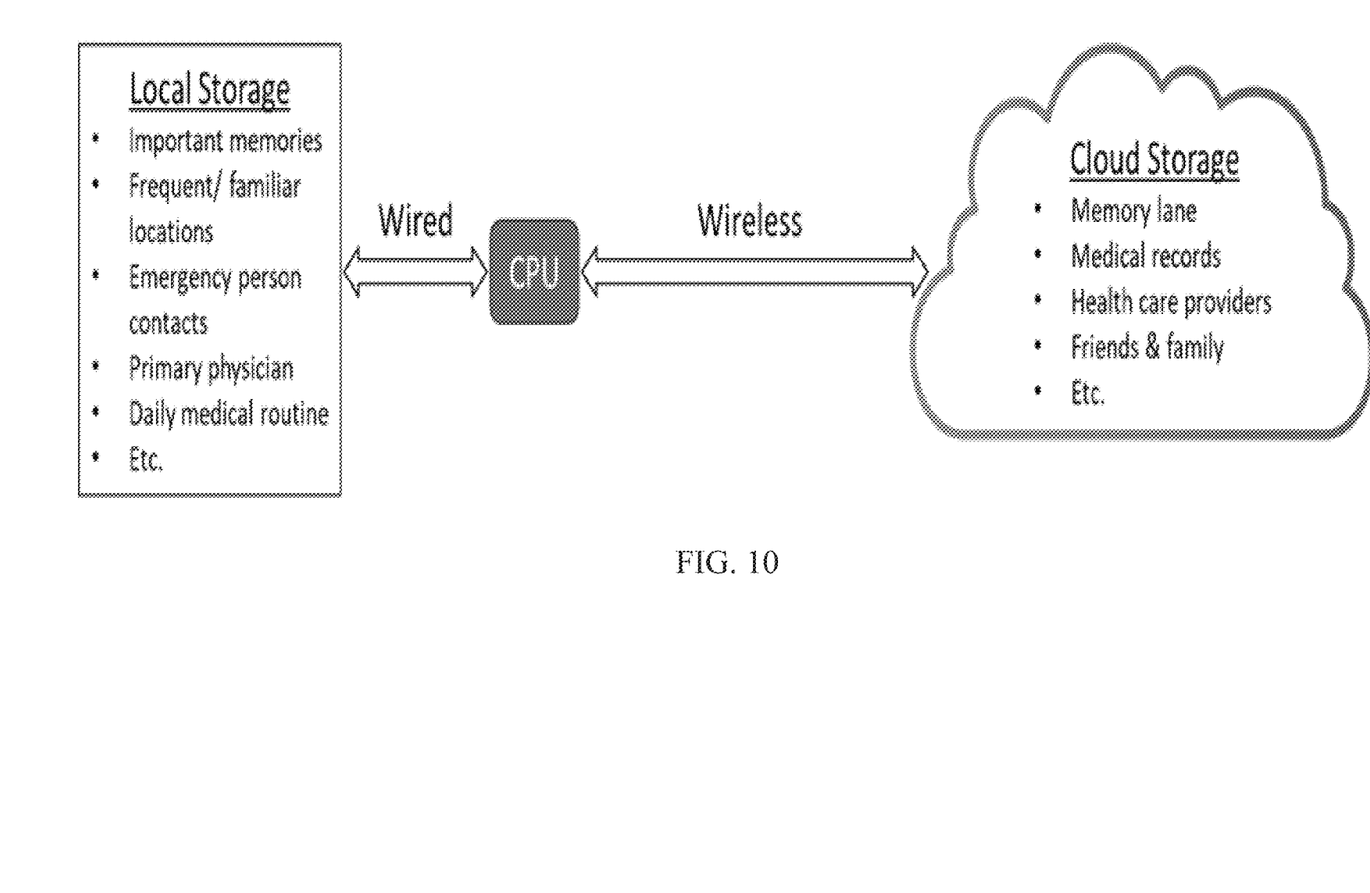
FIG. 10 shows a block diagram of data storage, locally and in the cloud, for a system for assisting individuals with certain ailments, according to an embodiment of the subject invention.

Data storage: The system can sort out total data into local and/or cloud storage, keeping the most valuable and necessary data (analyzed by AI/ML) in the local storage, thereby being prepared for the worst-case scenarios with no connectivity (wireless or wired) (see also FIG. 10).

The innovative and comprehensive systems and methods of embodiments of the subject invention use a combination of state-of-the-art sensors, AR technology, and ML algorithms to improve the lives of individuals with cognitive or visual impairments. By providing real-time information, assistance, and health monitoring, the system promotes independence, safety, and well-being, while also offering potential benefits to caregivers, healthcare providers, and insurance companies. As the population ages and the prevalence of dementia, Alzheimer's Disease, and visual impairments continues to rise, the system offers a promising and adaptable solution to help those in need.

Embodiments of the subject invention provide a focused technical solution to the focused technical problem of how to assist people with cognitive and/or visual impairments. The solution is provided by a combination of sensors, AR technology, and ML algorithms. The systems and methods of embodiments of the subject invention allow for significantly improved quality of life for users with cognitive and/or visual impairments.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

When ranges are used herein, combinations and subcombinations of ranges (including any value or subrange contained therein) are intended to be explicitly included. When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A system for assisting a subject with an ailment, the system comprising:
   at least one camera configured to capture real-time visual data of a surrounding area of the subject;
   at least one gyroscope configured to track orientation and movement of the subject;
   at least one augmented reality (AR) device configured to overlay customized real-time visual cues;
   at least one biometric sensor configured to continuously monitor physiological data of the subject;
   at least one microphone configured to capture audio;
   at least one haptic actuator configured to provide adaptive tactile feedback to the subject;
   at least one audio output device configured to deliver real-time audio to the subject, the at least one audio output device comprising at least one of headphones, a headset, and a set of earbuds;
   at least one processor in operable communication with the at least one camera, the at least one gyroscope, the at least one AR device, the at least one biometric sensor, the at least one microphone, the at least one haptic actuator, and the at least one audio output device; and
   a machine-readable medium in operable communication with the processor and having instructions stored thereon that, when executed by the processor, perform the following steps:
   a) receiving input data about the subject and the surrounding area of the subject, the input data comprising the real-time visual data received from the at least one camera, data received from the at least one gyroscope, the physiological data received from the at least one biometric sensor, and data received from the at least one microphone;
   b) utilizing a machine learning (ML) algorithm to process the input data and generate a context-aware, predictive action plan to assist the subject, the ML algorithm being trained on sensor fusion data, and the action plan dynamically adapts based on changes in the input data; and
   c) providing the action plan to the subject via:
      i) real-time AR visual cues provided to the subject by the at least one AR device;
      ii) audio feedback provided to the subject by the at least one audio output device; and
      iii) haptic feedback provided to the subject by the at least one haptic actuator, the haptic feedback comprising a vibration to alert the subject of an immediate risk in the surrounding area of the subject, and
   the utilizing of the ML algorithm in step b) comprising:
      detecting any deviation from an expected behavior pattern of the subject using a first long short-term memory (LSTM) recurrent neural network (RNN) trained on previous behavior data of the subject;
      using a first convolutional neural network (CNN) on the real-time visual data received from the at least one camera to assess the surrounding area of the subject;
      using a second RNN to manage time series data of the input data to assess the surrounding area of the subject;
      using a second CNN trained on a dataset of labeled facial images to perform facial recognition on any people within the surrounding area of the subject;
      using a time series analysis technique to detect patterns and trends in the data received from the at least one biometric sensor to keep track of the ailment of the subject; and
      adaptively adjusting the action plan using reinforcement learning (RL) based on preferences of the subject.

2. The system according to claim 1, further comprising:
   an accelerometer in operable communication with the processor; and
   a heart rate sensor in operable communication with the processor,
   the input data further comprising data received from the accelerometer and data received from the heart rate sensor.

3. The system according to claim 1, further comprising at least one global positioning system (GPS) sensor in operable communication with the processor,
   the input data further comprising data received from the at least one GPS sensor.

4. The system according to claim 1, the instructions when executed further performing the following step:
   d) transmitting, to an insurance company, at least one of: the input data; and output data generated by the ML model based on the analyzing of at least one of objects, people, conditions, and events in the surrounding area of the subject.

5. The system according to claim 1, the action plan being an action plan for at least one of wayfinding, social interaction, situational awareness, health monitoring, emotional state management, and medication and appointment management.

6. A method for assisting a subject with an ailment, the method comprising:
   a) receiving input data about the subject and a surrounding area of the subject, the input data comprising real-time visual data received from at least one camera, data received from at least one gyroscope, physiological data received from at least one biometric sensor, and data received from at least one microphone;
   b) utilizing a machine learning (ML) algorithm to process the input data and generate a context-aware, predictive action plan to assist the subject, the ML algorithm being trained on sensor fusion data and the action plan dynamically adapting based on changes in the input data; and
   c) providing the action plan to the subject via:
      i) real-time AR visual cues provided to the subject by at least one augmented reality (AR) device;
      ii) audio feedback provided to the subject by at least one audio output device; and
      iii) haptic feedback provided to the subject by at least one haptic actuator, the haptic feedback comprising a vibration to alert the subject of an immediate risk in the surrounding area of the subject, the at least one camera being configured to capture the real-time visual data of the surrounding area of the subject;
the at least one gyroscope being configured to track orientation and movement of the subject;
the at least one AR device being configured to overlay customized real-time visual cues;
the at least one biometric sensor being configured to continuously monitor the physiological data of the subject;
the at least one microphone being configured to capture audio;
the at least one haptic actuator being configured to provide adaptive tactile feedback to the subject;
the at least one audio output device being configured to deliver real-time audio to the subject,
the at least one audio output device comprising at least one of headphones, a headset, and a set of earbuds, and
the utilizing of the ML algorithm in step b) comprising:
   detecting any deviation from an expected behavior pattern of the subject using a first long short-term memory (LSTM) recurrent neural network (RNN) trained on previous behavior data of the subject;
   using a first convolutional neural network (CNN) on the real-time visual data received from the at least one camera to assess the surrounding area of the subject;
   using a second RNN to manage time series data of the input data to assess the surrounding area of the subject;
   using a second CNN trained on a dataset of labeled facial images to perform facial recognition on any people within the surrounding area of the subject;
   using a time series analysis technique to detect patterns and trends in the data received from the at least one biometric sensor to keep track of the ailment of the subject; and
   adaptively adjusting the action plan using reinforcement learning (RL) based on preferences of the subject.

7. The method according to claim 6, the input data further comprising data received from at least one global positioning system (GPS) sensor.

8. The method according to claim 6, the input data further comprising data received from an accelerometer and data received from a heart rate sensor.

9. The method according to claim 6, further comprising:
d) transmitting, to an insurance company, at least one of: the input data; and output data generated by the ML model based on the analyzing of at least one of objects, people, conditions, and events in the surrounding area of the subject.

10. The method according to claim 6, the action plan being an action plan for at least one of wayfinding, social interaction, situational awareness, health monitoring, emotional state management, and medication and appointment management.

11. The method according to claim 6, the ailment being dementia, Alzheimer's disease, or visual impairment.

12. A system for assisting a subject with an ailment, the system comprising:
at least one camera configured to capture real-time visual data of a surrounding area of the subject;
at least one gyroscope configured to track orientation and movement of the subject;
at least one augmented reality (AR) device configured to overlay customized real-time visual cues;
at least one biometric sensor configured to continuously monitor physiological data of the subject;
at least one microphone configured to capture audio;
an accelerometer;
a heart rate sensor;
at least one audio output device configured to deliver real-time audio to the subject, the at least one audio output device comprising at least one of headphones, a headset, and a set of earbuds;
at least one haptic actuator configured to provide adaptive tactile feedback to the subject;
at least one global positioning system (GPS) sensor;
at least one processor in operable communication with the at least one camera, the at least one gyroscope, the at least one AR device, the at least one biometric sensor, the at least one microphone, the accelerometer, the heart rate sensor, the at least one audio output device, the at least one haptic actuator, and the at least one GPS sensor; and
a machine-readable medium in operable communication with the processor and having instructions stored thereon that, when executed by the processor, perform the following steps:
a) receiving input data about the subject and the surrounding area of the subject, the input data comprising the real-time visual data received from the at least one camera, data received from the at least one gyroscope, the physiological data received from the at least one biometric sensor, data received from the at least one microphone, data received from the accelerometer, data received from the heart rate sensor, and data received from the at least one GPS sensor;
b) utilizing a machine learning (ML) algorithm to process the input data and generate a context-aware, predictive action plan to assist the subject, the ML algorithm being trained on sensor fusion data, and the action plan dynamically adapts based on changes in the input data;
c) providing the action plan to the subject via:
i) real-time AR visual cues provided to the subject by the at least one AR device;
ii) audio feedback provided to the by the at least one audio output device; and
iii) haptic feedback provided to the subject by the at least one haptic actuator, the haptic feedback comprising a vibration to alert the subject of an immediate risk in the surrounding area of the subject,
the action plan being an action plan for at least one of wayfinding, social interaction, situational awareness, health monitoring, emotional state management, and medication and appointment management, and
the utilizing of the ML algorithm in step b) comprising:
   detecting any deviation from an expected behavior pattern of the subject using a first long short-term memory (LSTM) recurrent neural network (RNN) trained on previous behavior data of the subject;
   using a first convolutional neural network (CNN) on the real-time visual data received from the at least one camera to assess the surrounding area of the subject;
   using a second RNN to manage time series data of the input data to assess the surrounding area of the subject;
   using a second CNN trained on a dataset of labeled facial images to perform facial recognition on any people within the surrounding area of the subject;

using a time series analysis technique to detect patterns and trends in the data received from the at least one biometric sensor to keep track of the ailment of the subject; and adaptively adjusting the action plan using reinforcement learning (RL) based on preferences of the subject.

13. The system according to claim 12, the instructions when executed further performing the following step:

d) transmitting, to an insurance company, at least one of: the input data; and output data generated by the ML model based on the analyzing of at least one of objects, people, conditions, and events in the surrounding area of the subject.

* * * * *